US009719943B2

(12) United States Patent
Horn (10) Patent No.: US 9,719,943 B2
(45) Date of Patent: Aug. 1, 2017

(54) WAFER EDGE INSPECTION WITH TRAJECTORY FOLLOWING EDGE PROFILE

(71) Applicant: KLA-TENCOR CORPORATION, Milpitas, CA (US)

(72) Inventor: Paul Horn, Milpitas, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 33 days.

(21) Appl. No.: 14/865,457

(22) Filed: Sep. 25, 2015

(65) Prior Publication Data

US 2016/0091437 A1 Mar. 31, 2016

Related U.S. Application Data

(60) Provisional application No. 62/057,240, filed on Sep. 30, 2014.

(51) Int. Cl.
G01N 21/00 (2006.01)
G01N 21/95 (2006.01)

(52) U.S. Cl.
CPC .............................. G01N 21/9503 (2013.01)

(58) Field of Classification Search
CPC .......... G01N 21/9503; G01N 21/8806; G01N 21/8851; H04L 1/1825; H04L 1/188
USPC ...................... 356/237.1–237.6, 239.1–239.8
See application file for complete search history.

(56) References Cited

U.S. PATENT DOCUMENTS

| 7,532,318 B2 | 5/2009 | Meeks et al. |
| 7,593,565 B2 | 9/2009 | Reich et al. |
| 7,656,519 B2 | 2/2010 | Meeks et al. |
| 7,835,566 B2 | 11/2010 | Reich et al. |
| 8,426,223 B2 | 4/2013 | Voges et al. |
| 8,492,178 B2 | 7/2013 | Carlson et al. |
| 2001/0023927 A1 | 9/2001 | Hazelton |
| 2005/0013476 A1 | 1/2005 | Simpkins |
| 2005/0036671 A1 | 2/2005 | Watkins et al. |
| 2006/0054608 A1 | 3/2006 | Cahill et al. |
| 2007/0057164 A1 | 3/2007 | Vaughnn et al. |
| 2008/0013822 A1 | 1/2008 | Pai et al. |
| 2009/0059236 A1 | 3/2009 | Meeks et al. |

(Continued)

FOREIGN PATENT DOCUMENTS

| JP | 2013093389 A | 5/2013 |
| WO | 2009127574 A1 | 10/2009 |
| WO | 2010015695 A1 | 2/2010 |

OTHER PUBLICATIONS

International Search Report, PCT/US2015/053325, ISA/KR, Apr. 7, 2016.

*Primary Examiner* — Tri T Ton
(74) *Attorney, Agent, or Firm* — Hodgson Russ LLP (57) ABSTRACT

This inspection system has an optical head, a support system, and a controller in electrical communication with the support system. The support system is configured to provide movement to the optical head with three degrees of freedom. The controller is programmed to control movement of the optical head using the support system such that the optical head maintains a constant angle of incidence relative to a wafer surface while imaging a circumferential edge of the wafer. An edge profiler may be scanned across the wafer to determine an edge profile. A trajectory of the optical head can be determined using the edge profile.

14 Claims, 9 Drawing Sheets

(56) References Cited

U.S. PATENT DOCUMENTS

| | | |
|---|---|---|
| 2009/0161094 A1* | 6/2009 | Watkins ................ G06T 7/0004 356/237.2 |
| 2009/0196489 A1 | 8/2009 | Le |
| 2009/0296090 A1 | 12/2009 | Saha et al. |
| 2009/0306941 A1 | 12/2009 | Kotelyanskii et al. |
| 2010/0012855 A1 | 1/2010 | Lazarov et al. |
| 2011/0058174 A1 | 3/2011 | Ramachandran et al. |
| 2011/0199480 A1 | 8/2011 | Lev et al. |
| 2013/0022260 A1 | 1/2013 | Pai et al. |
| 2013/0100441 A1 | 4/2013 | Tagawa et al. |
| 2014/0063799 A1 | 3/2014 | Voges et al. |

* cited by examiner

WAFER EDGE INSPECTION WITH TRAJECTORY FOLLOWING EDGE PROFILE

CROSS-REFERENCE TO RELATED APPLICATIONS

This application claims priority to the provisional patent application filed Sep. 30, 2014 and assigned U.S. application Ser. No. 62/057,240, the disclosure of which is hereby incorporated by reference.

FIELD OF THE DISCLOSURE

This disclosure relates to wafer edge inspection.

BACKGROUND OF THE DISCLOSURE

Wafers used in semiconductor manufacturing are typically inspected for defects such as, for example, surface imperfections, particles, or irregularities in thickness. These defects may impair operation of a semiconductor device. As each wafer processing step is expensive, manufacturers usually inspect the wafer between processing steps to determine whether the wafer should be reworked or scrapped.

Edges of a wafer can pose challenges during semiconductor manufacturing or inspection. Semiconductor manufacturers try to include as many semiconductor devices on a wafer as possible. Thus, inspection of the wafer edge may be needed to determine whether the edge can form usable devices. Devices near the wafer edge also may be inspected to determine yield or process control problems. However, wafer edges may be rounded or have irregular shapes. These rounded or irregular shaped edges can make inspection difficult.

Use of a semicircular scan of the wafer edge may result in images that are out of focus or unclear because the wafer edge may have an irregular, rather than perfectly semicircular, shape. This results in the optical head used for imaging being off-normal or defocused with respect to the edge profile over portions of the wafer surface or edge. For example, phase imaging over an irregular surface with a semicircular scan can result in a signal that is degraded by light and dark bands caused by variations in the angle of incidence of the imaging beam or defocus. Thus, sensitivity to defects is degraded.

Therefore, what is needed is an improved wafer edge inspection system and technique.

BRIEF SUMMARY OF THE DISCLOSURE

In a first embodiment, an inspection system is provided. The inspection system includes an optical head, a support system, and a controller. The support system is configured to provide movement to the optical head with three degrees of freedom around a circumferential edge of the wafer. The controller is in electrical communication with the support system and is programmed to control movement of the optical head using the support system such that the optical head maintains a constant angle of incidence relative to a wafer surface while imaging the circumferential edge of the wafer.

An edge profiler may be operatively connected to the controller. The edge profiler may be a shadowgram imaging system that includes a collimated light source and a camera. The camera is configured to receive collimated light from the collimated light source and image a shadow of the circumferential edge of the wafer.

The optical head may include an imaging system. The optical head may further include an edge profiler.

The controller may be configured to move the optical head from a first surface of the wafer to a second surface of a wafer.

The support system may be configured to move the optical head in a direction perpendicular to the wafer surface. The support system may be configured to move the optical head in a direction radially with respect to the wafer. The support system may be configured to rotate the optical head about an axis which is tangential with respect to the circumferential edge.

The inspection system may include a platen configured to support the wafer. The platen may be configured to rotate the wafer about a central axis of the wafer.

In a second embodiment, a method is provided. The method includes collecting and analyzing a shadowgram edge profile image of a wafer to determine an edge profile, determining a trajectory of an optical head using the edge profile, moving the optical head along the trajectory, and generating an image of the circumferential edge of the wafer. The shadowgram edge profile image is a shadow of a circumferential edge of the wafer generated using collimated light. A constant angle of incidence is maintained relative to a wafer surface while imaging a circumferential edge of the wafer using the trajectory. Images may be generated as a sum and difference of two individually orthogonally-polarized reflected incident beams. The imaging may be between a first surface of the wafer to an opposite second surface of the wafer.

In a third embodiment, a system is provided. The system includes a processor, a storage device in electronic communication with the processor, and a communication port in electronic communication with the processor. The processor is programmed to receive a shadowgram edge profile of a wafer, determine a trajectory of an optical head using the edge profile, and send instructions to move the optical head along the trajectory. The shadowgram edge profile image is a shadow of a circumferential edge of the wafer generated using collimated light. A constant angle of incidence is maintained relative to a wafer surface while imaging a circumferential edge of the wafer using the trajectory. The imaging may be between a first surface of the wafer to an opposite second surface of the wafer.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

The profile of a wafer's circumferential edge may not be perfectly semicircular. To maintain a constant angle of incidence while scanning an edge of a wafer, such as between a first surface of the wafer and an opposite second surface of the wafer, an optical head according to the present disclosure uses a trajectory based on the edge profile of the wafer. The optical head has three degrees of freedom, thus enabling the optical head to move along this trajectory. Maintaining a constant angle of incidence by moving along this trajectory avoids or minimizes light and dark banding during sidescan imaging and improves focus. This results in improved ability to detect objects of interest, such as edge-bead removal (EBR) variations.

Figure 1:
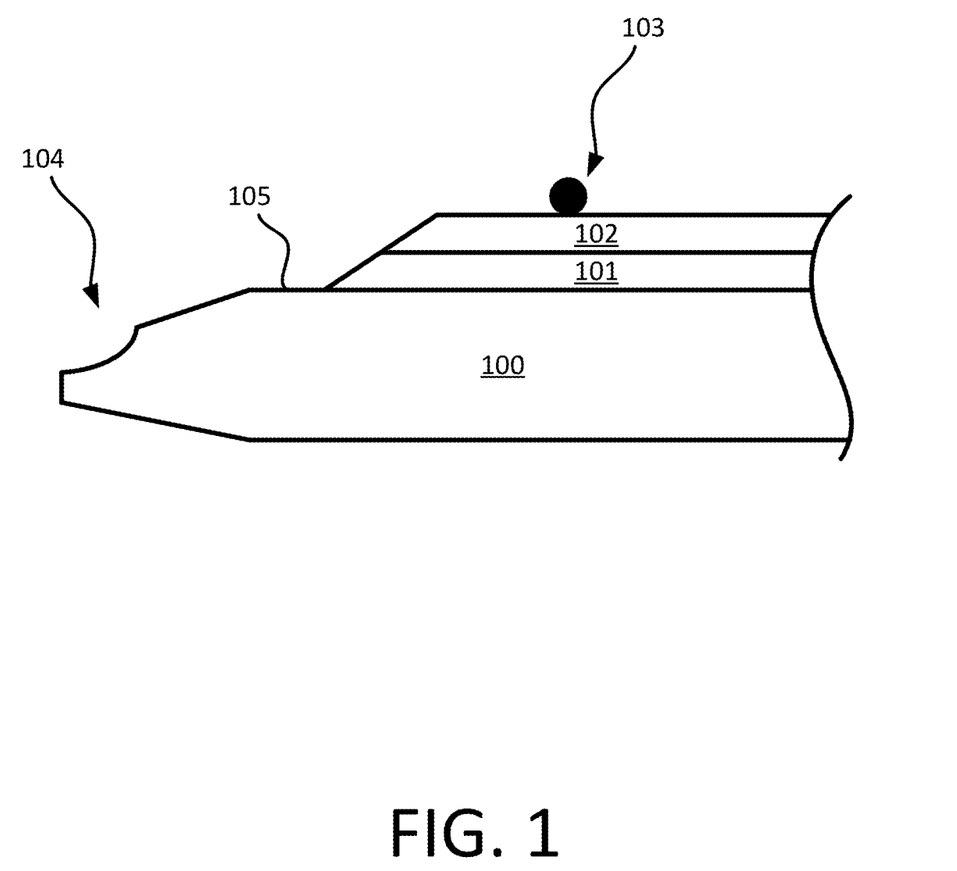
FIG. 1 is a cross-sectional diagram of a portion of an exemplary wafer showing possible defects.

FIG. 1 is a cross-sectional diagram of a portion of an exemplary wafer 100 showing examples of possible defects. Edge inspection may occur over the region seen in FIG. 1. The region seen in FIG. 1 is not an entirety of a cross-section of the wafer 100, but may be, for example, approximately 50% or less than 50% of the diameter of the wafer 100. The wafer can be Si, GaN, or other materials. The wafer 100 has two layers 101, 102 on the wafer surface 105. Layers 101, 102 may be conductive, semi-conductive, or non-conductive. These layers 101, 102 may be deposited on the wafer 100. The number of layers on the wafer 100 can vary. For example, zero layers, three layers, four layers, five layers, or more than five layers are possible. Some common defects include particles or debris 103, delamination of one or more of the layers 101, 102 from the surface 105 or each other, chips or scratches 104 at an edge of the wafer 100, or residue on a surface of the wafer 100.

Figure 2:
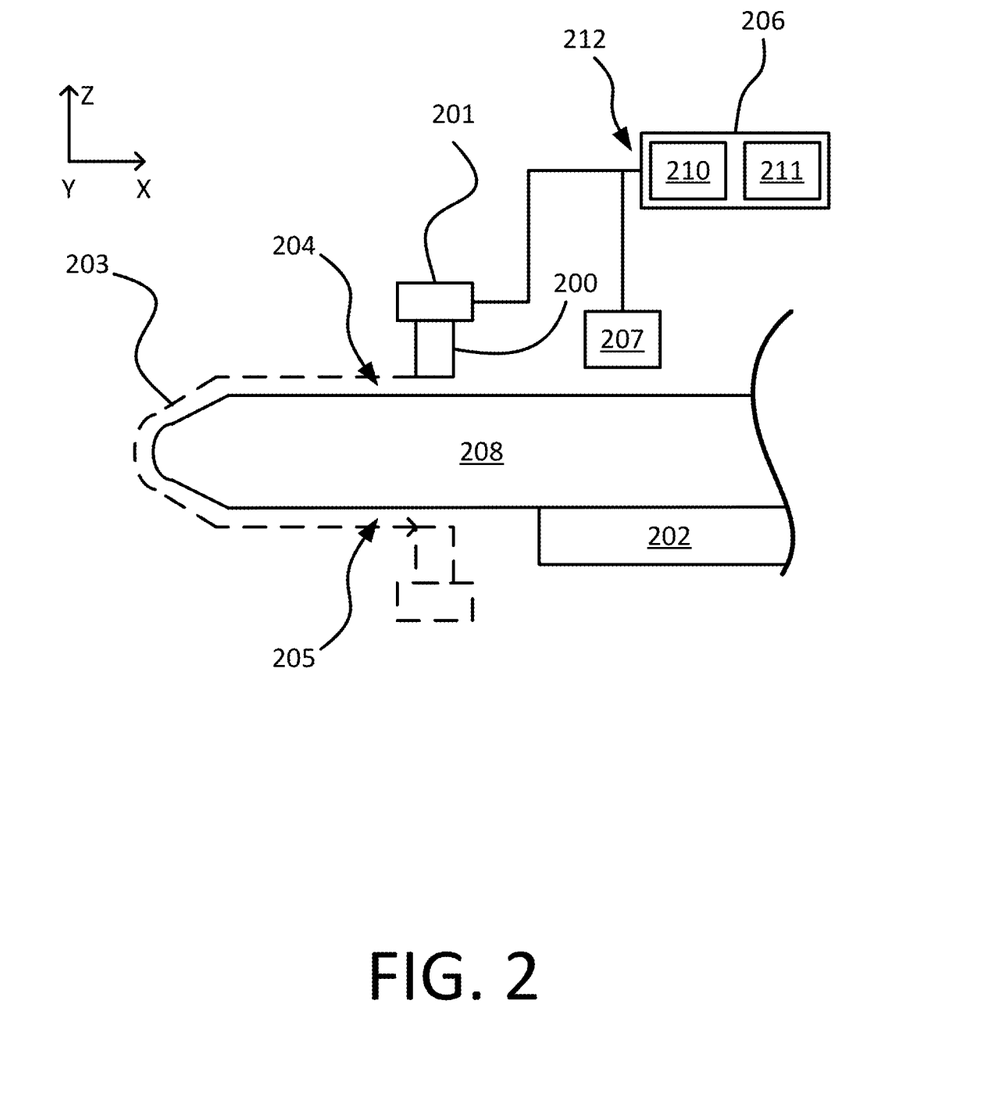
FIG. 2 is a diagram illustrating an embodiment of wafer inspection in accordance with the present disclosure.

A wafer 208 is inspected in FIG. 2. This wafer 208 may be the same as or different from the wafer 100 in FIG. 1. Thus, the wafer 208 may have one or more layers on the wafer surface or different circumferential edge shapes or configurations than that illustrated in FIG. 2.

The wafer 208 is positioned on a platen 202, which may be rotated about a central axis using a motor or other drive assembly. For example, the wafer 208 may be rotated in the X-Y plane.

The optical head 200 is connected to a support system 201 such as, for example, a frame. The optical head 200 is moved along a trajectory 203 (shown with a dotted line) between a first surface 204 and a second surface 205 of the wafer 208. A circumferential edge of the wafer 208 is imaged. This circumferential edge may be between the two opposite flat portions of the wafer 208. The wafer may be stationary or may be rotated about a central axis while the optical head 200 is moved along the trajectory 203. The trajectory 203 may approximately match the surfaces of the wafer 208 in an instance. The support system 201 is configured to provide movement to the optical head 200 with three degrees of freedom around a circumferential edge of the wafer 208. These three degrees of freedom enable the trajectory 203 around the circumferential edge to be irregular while simultaneously maintaining a constant angle of incidence relative to the wafer. Thus, the optical head 200 can move in more than just a semicircular trajectory.

The trajectory 203 may account for one or more layers (for example, as seen in FIG. 1) on a surface of the wafer 208. Thus, the edge profile of the wafer 208 may or may not include layers disposed on a surface of the wafer 208. Even if layers are present on a surface of the wafer, the edge profile may not include the layers because, for example, the edge profile only is for a portion of the wafer 208 where the layers are not present. Also, the trajectory may not include the thickness of the layers because the layers may be sufficiently thin that the trajectory is not significantly impacted. The trajectory 203 uses this edge profile.

Figure 3:
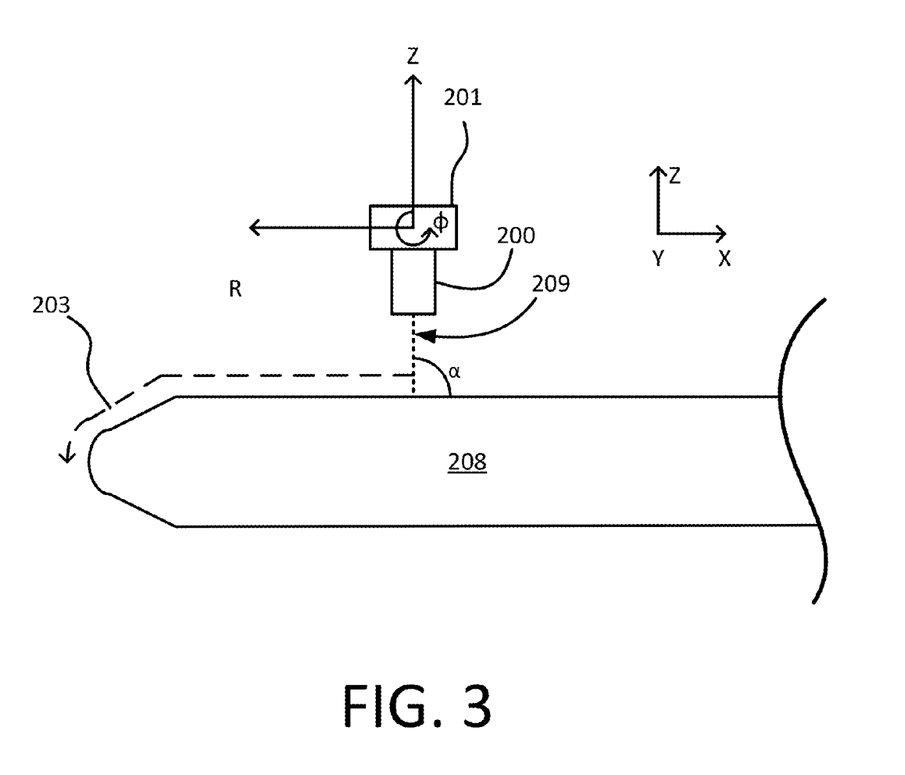
FIG. 3 is a diagram illustrating degrees of freedom during the wafer inspection of FIG. 2.

Turning to FIG. 3, support system 201 is configured to provide movement to the optical head 200 with three degrees of freedom. For example, the support system 201 can provide movement in the R (radial) and Z axes, which are perpendicular to one another. In one example, the R axis is parallel to a flat portion of the wafer 208 (e.g., the X-Y plane) and the Z axis is perpendicular to this flat portion of the wafer 208. Thus, the optical head 200 can be moved in a direction perpendicular to a surface of the wafer 208 and radially with respect to the wafer 208.

The support system 201 also can provide rotational movement about the Φ axis, which may be tangential to a circumferential edge of the wafer 208. Rotational movement about the Φ axis can change an angle of incidence α of the imaging path 209 relative to the wafer 208 or a surface of the wafer 208.

Turning back to FIG. 2, a controller 206 is operatively connected to the actuators of the support system 201. The controller 206 includes a processor 210, a storage device 211 in electronic communication with the processor 210, and a communication port 212 in electronic communication with the processor 210. It is to be appreciated that the controller 206 may be implemented in practice by any combination of hardware, software, and firmware. Also, its functions as described herein may be performed by one unit, or divided up among different components, each of which may be implemented in turn by any combination of hardware, software and firmware. Program code or instructions for the controller 206 to implement the various methods and functions described herein may be stored in controller readable storage media, such as a memory, within the controller 206, external to the controller 206, or combinations thereof.

The controller 206 is programmed to control movement of the optical head 200 using the support system 201 such that the optical head 200 maintains a constant angle of incidence relative to a wafer surface while imaging a circumferential edge of the wafer 208. This constant angle of incidence may be perpendicular to a surface of the wafer 208 or may be at an angle between 0° and 90° relative to a surface of the wafer 208. In an example, the optical head 200 may move radially from approximately 1 mm to 10's of mm, in the Z axis from less than approximately 0.05 mm to several mm, and in Φ by approximately 90° to 180° or more.

The controller 206 can control the distance between the optical head 200 and a surface of the wafer 208. This distance may be, for example, optimized for imaging or may remain constant during imaging. The optical head 200 may be positioned a distance from the surface of the wafer 208 from less than approximately 1 mm to 10's of mm.

The controller 206 also may be operatively connected to the optical head 200. The controller 206 may provide instructions for the optical head 200 to image the circumferential edge of the wafer 208.

The controller 206 is operatively connected to an edge profiler 207. This edge profiler 207 may be, for example, a shadowgram system. The edge profiler 207 can determine an edge profile of the wafer 208. The edge profiler 207 may be part of the optical head 200 or, for example, may be a standalone system.

Figure 4:
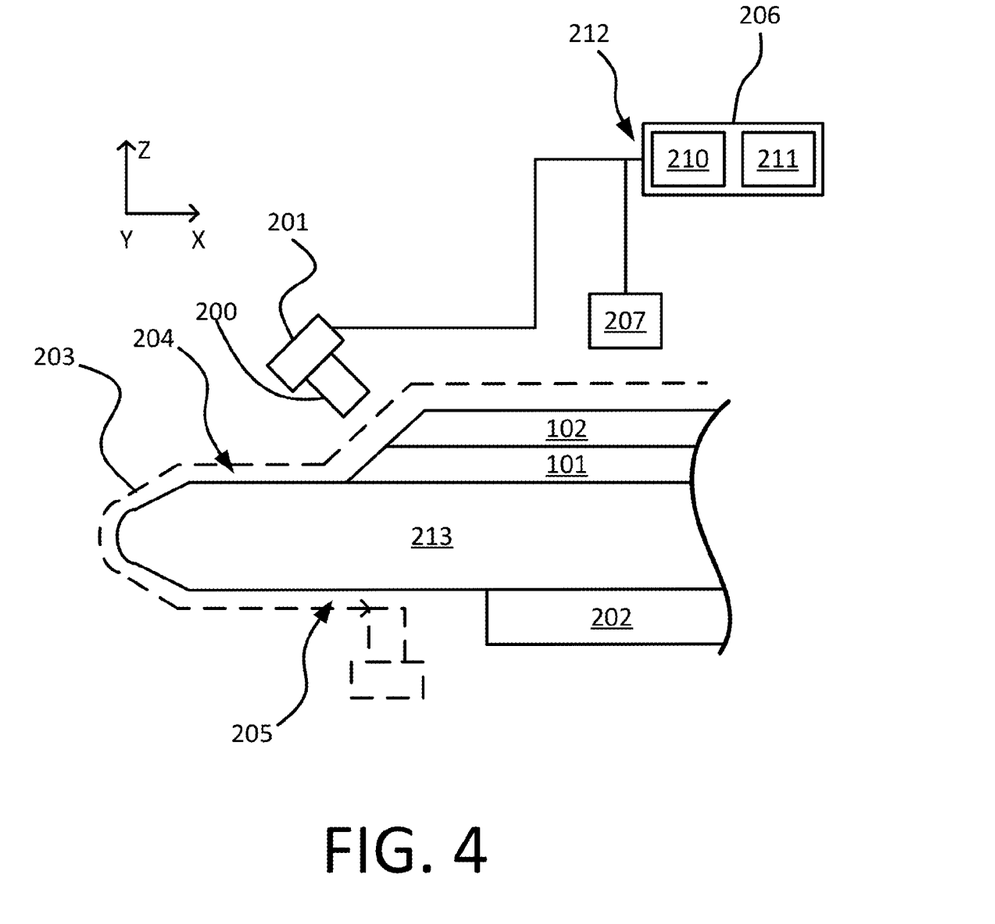
FIG. 4 is another diagram illustrating an embodiment of wafer inspection in accordance with the present disclosure.
Figure 5:
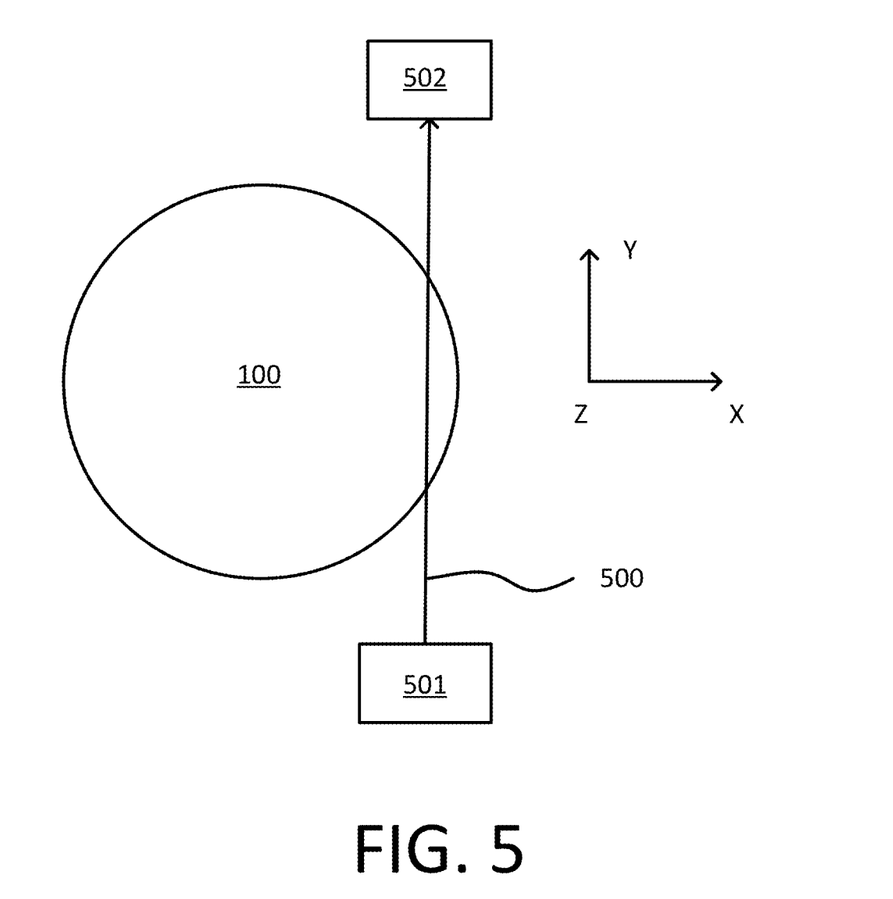
FIG. 5 is a top view of an edge profiler in accordance with the present disclosure.

A wafer 213 is inspected in FIG. 4. This wafer 213 may be the same as or different from the wafer 100 in FIG. 1. As seen in FIG. 4, the wafer 213 includes two layers 101, 102. The trajectory 203 accounts for the layers 101, 102 for movement of the optical head 200 as the optical head 200 maintains a constant angle of incidence relative to a wafer surface FIG. 5 is a top view of an edge profiler, such as the edge profiler used in the KLA-Tencor CV310i inspection system. This may be a shadowgram imaging system. In this example, a collimated light source 501 may generate a beam 500 intersecting the edge of the wafer 100, and a shadowgram of the edge of surface 100 may be imaged by camera 502.

Figure 6:
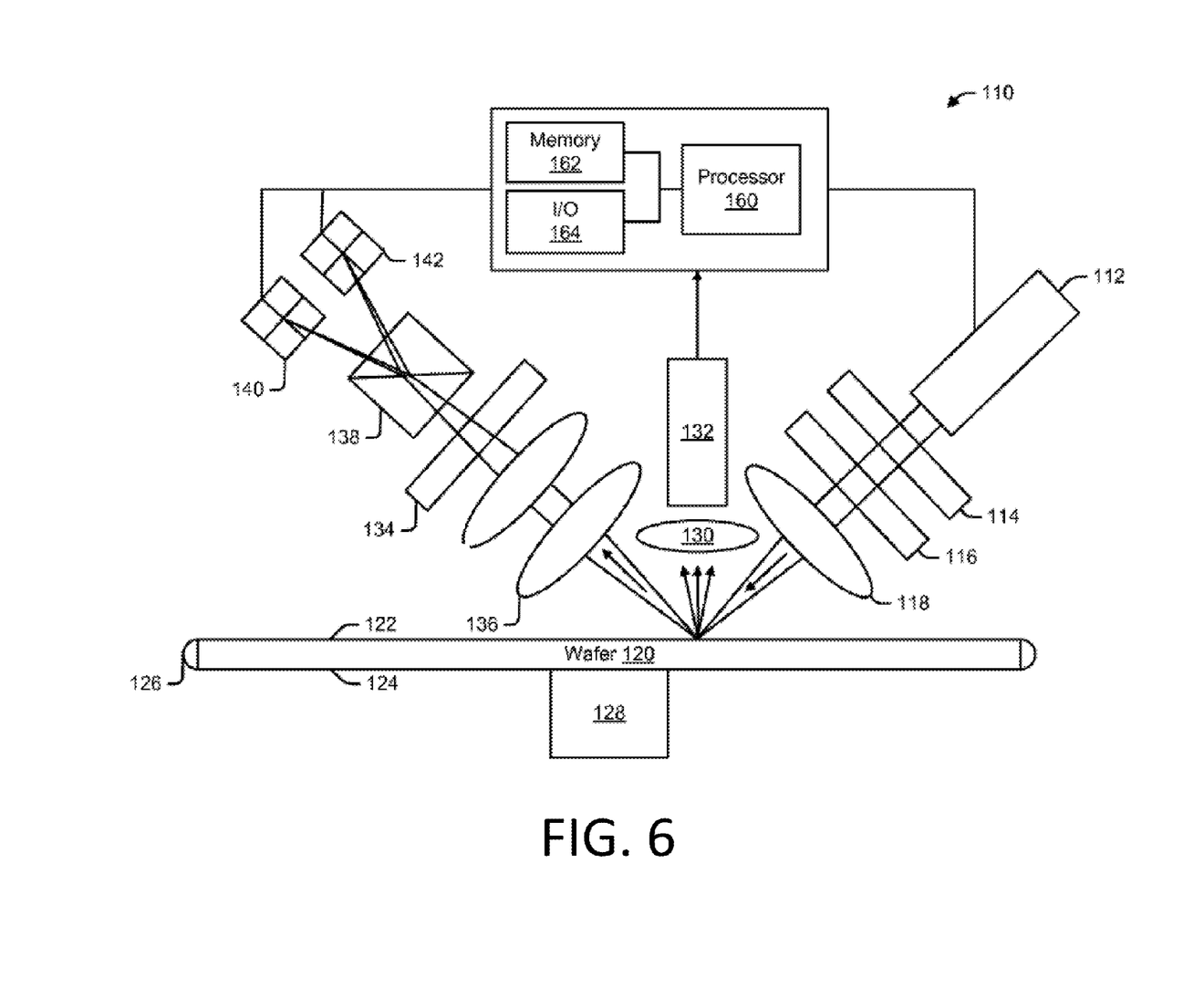
FIG. 6 a schematic illustration of optical components of an embodiment of an apparatus for wafer edge inspection in accordance with the present disclosure.

FIG. 6 a schematic illustration of optical components of an embodiment of an apparatus for wafer edge inspection. One embodiment is adapted to perform film thickness measurement, surface roughness measurement, reflectivity measurement, and/or optical profiling using radiation in the optical spectrum. In alternate embodiments radiation outside the visible optical spectrum may be used. More particularly, FIG. 6 depicts an optics assembly that includes a combined reflectometer and scatterometer. This embodiment is capable of detecting and classifying a wide variety of defects at or near a wafer's circumferential edge.

Wafer 120, which is positioned on a platen 128, includes an upper surface 122, a lower surface 124, and an edge surface 126, which may be substantially flat or curved when viewed in a cross-sectional profile. This wafer 120 may be the same as or different than the wafer 100 in FIG. 1, the wafer 208 in FIG. 2, or the wafer 213 in FIG. 4. In the embodiment depicted in FIG. 6, the wafer edge surface 126 is curved when viewed in cross-sectional profile.

A surface analyzer assembly 110 is positioned to direct radiation onto a surface of wafer 120. In the embodiment depicted in FIG. 6, surface analyzer assembly 110 includes a laser diode 112, an optional polarizer 114, an optional quarter-wave plate 116, and a focusing lens 118 for directing radiation onto a surface of wafer 120. These components target radiation from the laser diode 112 onto the surface of wafer 120, and hence may be considered a radiation targeting assembly. In alternative embodiment, the polarizer 114 and quarter-wave plate 116 may be omitted.

Surface analyzer assembly 110 further includes a collecting lens 130 and a photomultiplier tube (PMT) 132. These components collect radiation scattered by the surface of the wafer 120, and hence may be considered a scattered radiation assembly. In alterative embodiments the PMT 132 and collecting lens 130 may be replaced with an integrating sphere or an ellipsoidal mirror together with a PIN photodiode or avalanche photodiode.

Surface analyzer assembly 110 further includes a collimating lens 136, a quarter-wave plate 134, a polarizing beamsplitter 138, and two detectors such as PIN photodiodes 140 and 142. Additional lenses may also be included to reduce the motion of the beam on the detectors 140 and 142 caused by surface height deviations. In this embodiment, the angle of incidence of the laser beam to the surface is approximately 60 degrees. Other angles of incidence may also be used. The plane of incidence of the beam, defined as the plane containing both the incident beam and the reflected beam, is maintained perpendicular to the wafer surface at the tangent point of the laser spot, which an advantageous relationship for enhanced performance.

Focusing lens 118 creates a small spot on the surface of a wafer 120. The PMT 132 and collecting lens 130 are used to measure the scattered light for the purposes of computing the surface roughness, measuring debris, detecting stains, cracks, scratches, delamination, blisters or corrosion on the wafer 120 surface or at or near the circumferential edge 126.

After reflecting from the wafer, two orthogonally-polarized light samples are separated by the waveplate-beamsplitter combination with one beam each incident on detectors 140 and 142. These two signals can be either added or differenced to produce images which, in turn, allow defects or film edges to be identified and located.

The data collected by the scattered radiation collection assembly and the reflected radiation collection assembly is fed to a processing module that includes a processor 160, a memory module 162, and an I/O module 164. Processor module comprises logic instructions that enable the instrument described in FIG. 6 to simultaneously measure the S and P components of the reflectivity. The processor 160 may be the same as or different than the processor 210 in the controller 206.

While FIG. 6 illustrates optical components for an exemplary wafer edge inspection, various changes to these optical components or a different inspection or imaging system are possible.

Figure 7:
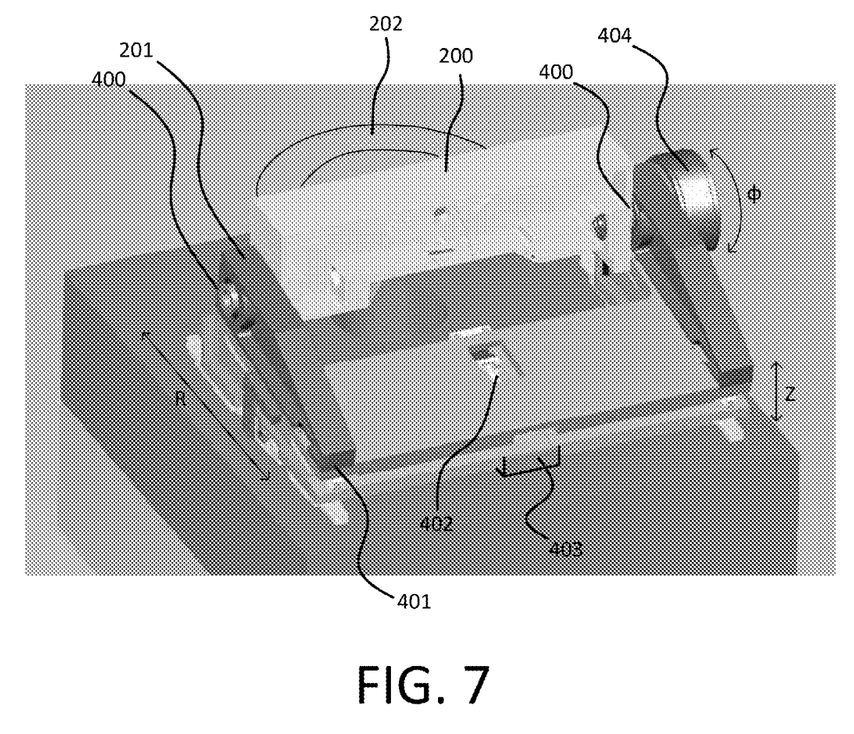
FIG. 7 is a perspective view of an embodiment of an optical head and support system in accordance with the present disclosure.

FIG. 7 is a perspective view of an embodiment of an optical head 200 and support system 201 in accordance with the present disclosure. The optical head 200 can move around a circumferential edge of a wafer positioned on the platen 202 (shown in outline).

The optical head 200 may include both the edge profiler and imaging system. The optical head 200 also may include the imaging system and the edge profiler can be a separate unit or standalone tool.

The optical head 200 may include some or all of the surface analyzer assembly 110 of FIG. 6. This surface analyzer assembly 110 is an example of an imaging system. Other imaging system designs are possible.

The optical head 200 is positioned between bearings 400. These two bearings 400 enable rotation of the optical head 200 to provide rotational movement in the Φ direction.

The support system 201 and/or base 401 of the support system 201 includes actuators 402, 403, and 404 that are used to move the optical head 200. The actuator 403 is shown in outline to represent its placement. The actuator 404 provides rotational movement about the Φ axis. The actuator 404 may be positioned in the support system 201, such as proximate a bearing 400. The actuators 402 and 403 provide translation in the Z and R directions. The actuators 402, 403, and 404 can operate in a cooperative manner, though not all actuators 402, 403, and 404 may be operating simultaneously during inspection.

The actuators 402, 403, and 404 may be servo motors, stepper motors, linear motors, or some other type of motor that can move the optical head 200. The actuators 402, 403, or 404 may include a gearing or transmission system. Embodiments may have fewer actuators. The actuators 402, 403, and 404 may be positioned in different locations from that illustrated in FIG. 7.

Figure 8:
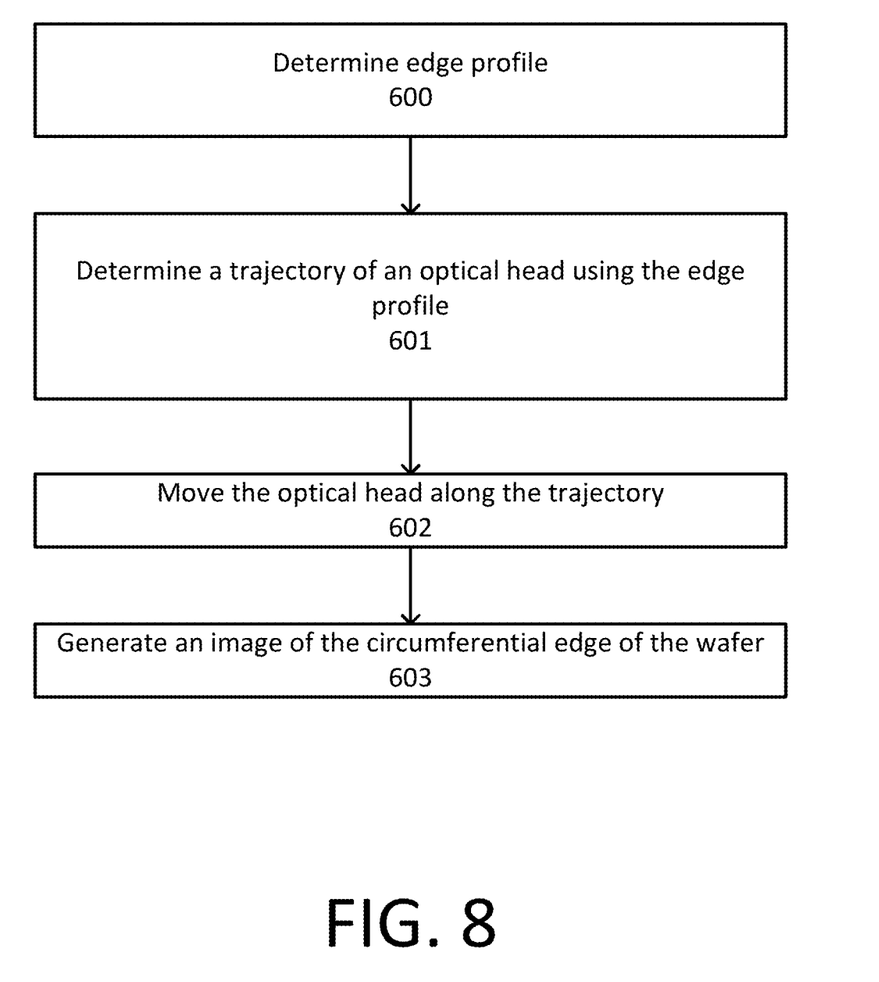
FIG. 8 is a flowchart in accordance with an embodiment of the present disclosure.

FIG. 8 is a flowchart in accordance with an embodiment of the present disclosure. In 600, an edge profile is determined. A shadowgram imaging system or another technique may be used to determine the edge profile.

The edge profile of the wafer may include an entire wafer surface or just part of the wafer surface. For example, the edge profile may be determined at a specified number of radial positions of the circumferential edge of the wafer. For example, a user may specify that the edge profile may be determined at between 1 and 25 radial positions of the circumferential edge of the wafer.

In 601, a trajectory of an optical head is determined using this edge profile. The trajectory may be unique to an individual wafer or may be adjusted from a standard trajectory to compensate for the particular edge profile of a wafer. The trajectory for a particular radial position of a wafer may be the same or different compared to another radial position of the wafer. Thus, the trajectory for the optical head may be the same for all radial positions of a wafer. The trajectory also may be different for some or all of the radial positions of a wafer.

In 602, the optical head is moved along the trajectory.

In 603, an image is generated of the circumferential edge using the optical head. The imaging may be between a first surface of the wafer and an opposite second surface of the wafer. These opposing surfaces may be the flat surfaces of the wafer. Images can be generated as a sum and difference of two individually orthogonally-polarized reflected incident beams.

Figure 9:
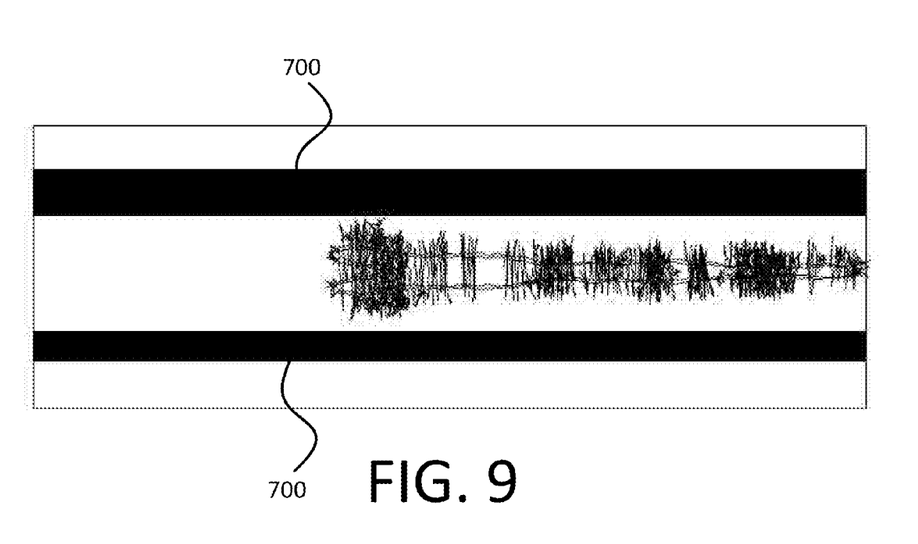
FIG. 9 is a rendering of an exemplary sidescan image with banding.
Figure 10:
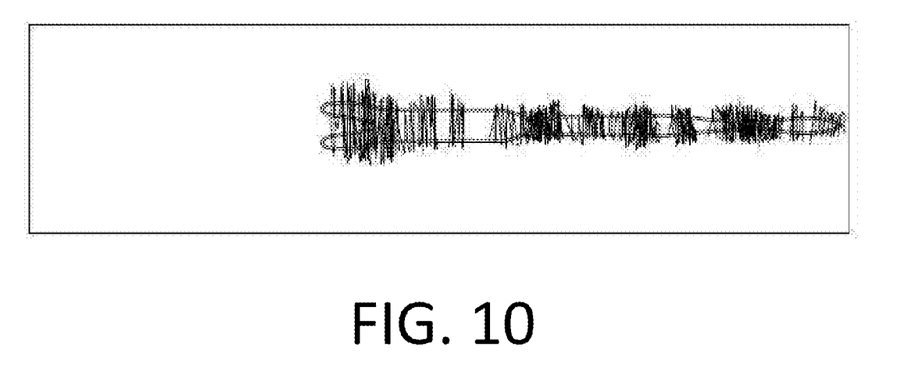
FIG. 10 is a rendering of an exemplary sidescan image without banding intending to convey improved focus compared to FIG. 9.

A sensitive detection signal for thin films is an image constructed by subtracting P-polarized reflected light from S-polarized reflected light (referred to herein as a phase image). Phase images are degraded on non-circular wafer profiles by defocus and/or by light and dark bands caused by variations in the angle of incidence of the beam to the surface of the wafer. Thus, sensitivity is also degraded. FIG. 9 is a rendering of an exemplary sidescan image with such banding 700 and defocus. Other banding of various shades or degrees may be present besides or instead of the banding 700. FIG. 10 is a rendering of an exemplary sidescan image without banding and with improved focus due to use of an embodiment disclosed herein. As will be readily apparent in a comparison between FIG. 9 and FIG. 10, FIG. 10 has improved focus and/or clarity and lacks the bands 700 of FIG. 9. For example, the edges in FIG. 10 are less blurry than in FIG. 9. The improved image that results from use of an embodiment disclosed herein can improve wafer inspection and/or increase sensitivity of wafer inspection.

The system and method described herein may be used for inspection of any type of wafer. The wafer may be a semiconductor wafer or stack of wafers, but also may be another type of wafer, such as those used to manufacture LEDs, solar cells, magnetic discs, flat panels, or polished plates. Other objects also may be inspected, as is known to those skilled in the art.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. An inspection system comprising:
   an optical head;
   a support system configured to provide movement to the optical head with three degrees of freedom around a circumferential edge of the wafer;
   a controller in electrical communication with the support system, the controller being programmed to control movement of the optical head using the support system such that the optical head maintains a constant angle of incidence relative to a wafer surface while imaging the circumferential edge of the wafer; and
   an edge profiler operatively connected to the controller, wherein the edge profiler is a shadowgram imaging system that includes a collimated light source and a camera, wherein the camera is configured to receive collimated light from the collimated light source and image a shadow of the circumferential edge of the wafer.

2. The inspection system of claim 1, wherein the optical head comprises an imaging system.

3. The inspection system of claim 2, wherein the optical head further comprises the edge profiler.

4. The inspection system of claim 1, wherein the controller is configured to move the optical head from a first surface of the wafer to a second surface of a wafer.

5. The inspection system of claim 1, wherein the support system is configured to move the optical head in a direction perpendicular to the wafer surface.

6. The inspection system of claim 1, wherein the support system is configured to move the optical head in a direction radially with respect to the wafer.

7. The inspection system of claim 1, wherein the support system is configured to rotate the optical head about an axis which is tangential with respect to the circumferential edge.

8. The inspection system of claim 1, further comprising a platen configured to support the wafer.

9. The inspection system of claim 8, wherein the platen is configured to rotate the wafer about a central axis of the wafer.

10. A method comprising:
    collecting and analyzing a shadowgram edge profile image of a wafer to determine an edge profile, wherein the shadowgram edge profile image is a shadow of a circumferential edge of the wafer generated using collimated light;
    determining a trajectory of an optical head using the shadowgram edge profile, wherein a constant angle of incidence is maintained relative to a wafer surface while imaging a circumferential edge of the wafer using the trajectory;
    moving the optical head along the trajectory; and
    generating an image of the circumferential edge of the wafer.

11. The method of claim 10, wherein images are generated as a sum and difference of two individually orthogonally-polarized reflected incident beams.

12. The method of claim 10, wherein the imaging is between a first surface of the wafer to an opposite second surface of the wafer.

13. A system comprising:
    a processor;
    a storage device in electronic communication with the processor; and
    a communication port in electronic communication with the processor;
    wherein the processor is programmed to:

receive a shadowgram edge profile of a wafer, wherein the shadowgram edge profile image is a shadow of a circumferential edge of the wafer generated using collimated light;

determine a trajectory of an optical head using the shadowgram edge profile, wherein a constant angle of incidence is maintained relative to a wafer surface while imaging a circumferential edge of the wafer using the trajectory; and send instructions to move the optical head along the trajectory.

14. The system of claim 13, wherein the imaging is between a first surface of the wafer to an opposite second surface of the wafer.

* * * * *